(12) United States Patent
Metelski

(10) Patent No.: US 6,708,936 B2
(45) Date of Patent: Mar. 23, 2004

(54) STAND, IN PARTICULAR FOR SURGICAL MICROSCOPES

(75) Inventor: Andrzej Metelski, Romanshorn (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 10/010,103

(22) Filed: Nov. 8, 2001

(65) Prior Publication Data

US 2002/0121579 A1 Sep. 5, 2002

(30) Foreign Application Priority Data

Nov. 12, 2000 (DE) .................................. 200 19 109 U

(51) Int. Cl.[7] .............................. A47F 5/00; A47F 7/00; F16M 11/00; F16M 13/00
(52) U.S. Cl. ............................... 248/123.11; 248/162.1; 248/280.11
(58) Field of Search .................. 248/123.11, 123.2, 248/162.1, 280.11, 585, 648, 127

(56) References Cited

U.S. PATENT DOCUMENTS

| 3,773,296 | A | * | 11/1973 | McKendrick | ............. | 137/116.5 |
|---|---|---|---|---|---|---|
| 3,880,393 | A | * | 4/1975 | Watson | ....................... | 248/325 |
| 4,277,044 | A | * | 7/1981 | Hamilton | ................ | 248/123.11 |
| 4,344,595 | A | * | 8/1982 | Heller et al. | ............. | 248/123.2 |
| 4,815,832 | A | * | 3/1989 | Nagano et al. | ......... | 248/123.11 |
| 5,037,267 | A | * | 8/1991 | Warner et al. | .............. | 248/324 |
| 5,173,802 | A | * | 12/1992 | Heller | ......................... | 359/384 |
| 5,196,422 | A | * | 3/1993 | Colerick Bird et al. | . | 514/252.05 |
| 5,205,522 | A | * | 4/1993 | Nakamura | ............. | 248/123.11 |
| 5,242,142 | A | * | 9/1993 | Nakamura | ............. | 248/280.11 |
| 5,253,832 | A | | 10/1993 | Bolas et al. | | |
| 5,257,998 | A | * | 11/1993 | Ota et al. | .................... | 414/917 |
| 5,397,323 | A | | 3/1995 | Taylor et al. | | |
| 5,613,419 | A | * | 3/1997 | Pierson et al. | ............... | 177/212 |
| 5,825,536 | A | * | 10/1998 | Yasunaga et al. | ....... | 248/123.11 |
| 6,050,530 | A | * | 4/2000 | Nakamura | ................ | 248/123.2 |
| 6,070,839 | A | | 6/2000 | Brenner et al. | | |
| 6,105,909 | A | * | 8/2000 | Wirth et al. | ............. | 248/123.2 |
| 6,106,511 | A | * | 8/2000 | Jensen | ......................... | 600/102 |
| 6,199,812 | B1 | * | 3/2001 | Schuepbach | ........... | 248/123.11 |
| 6,364,268 | B1 | * | 4/2002 | Metelski | .................. | 248/278.1 |

FOREIGN PATENT DOCUMENTS

| DD | 221 571 A1 | 4/1985 |
|---|---|---|
| DE | 3739080 A1 | 11/1989 |
| DE | 197 42 050 A1 | 3/1999 |
| EP | 0 433 426 B1 | 2/1994 |
| WO | WO 97/13997 | 10/1995 |
| WO | WO 99/01693 | 6/1997 |

OTHER PUBLICATIONS

Hilpert, Dipl.–Ing, "Weight Compensation In Precision Mechanical Devices", communication from the Instutut für Getriebetechnik Of Hochschule für Elektrotechnik Ilmenau (Dipl.–Ing A. Bock, Director), Feingerätetechnik vol. 14, No. 2(1965) pp. 61–66. (Translation attached).

* cited by examiner

Primary Examiner—Ramon O. Ramirez
Assistant Examiner—Amy J. Sterling
(74) Attorney, Agent, or Firm—Hodgson Russ LLP

(57) ABSTRACT

A stand having a carrier (2) and a load-equalizing unit (18), in the case of which stand there is provided, between the load-equalizing unit (18) and the support arm (2), a counterbalancing transmission (106) at which, independently of the position of the load, it is possible by means of changing the position of a connecting arm (5) for a constant force (FA) output by the load-equalizing unit (18) to be changed in position for balancing purposes when there are changes in weight at the load (G).

26 Claims, 5 Drawing Sheets

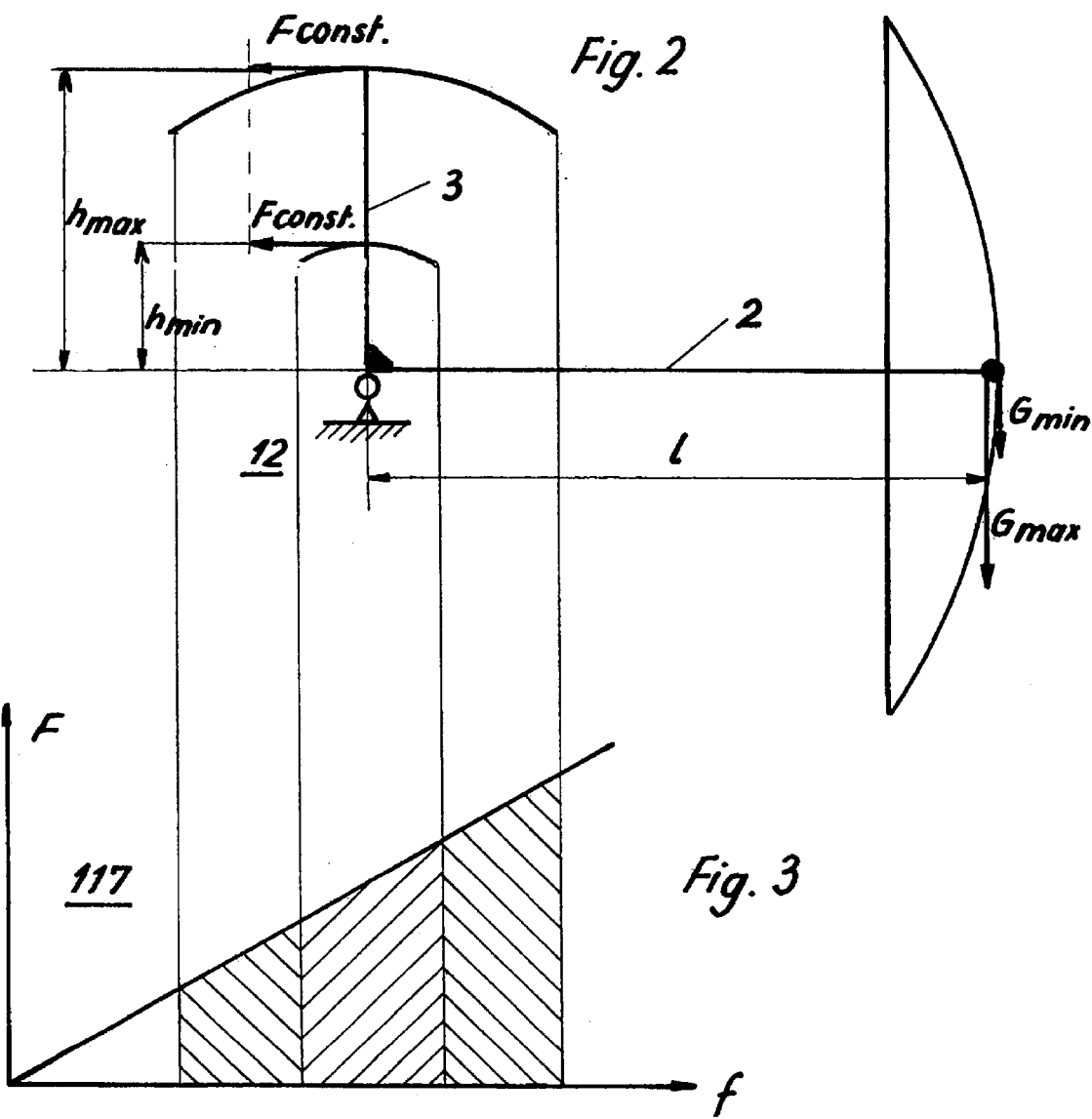
Fig. 2
Fig. 3
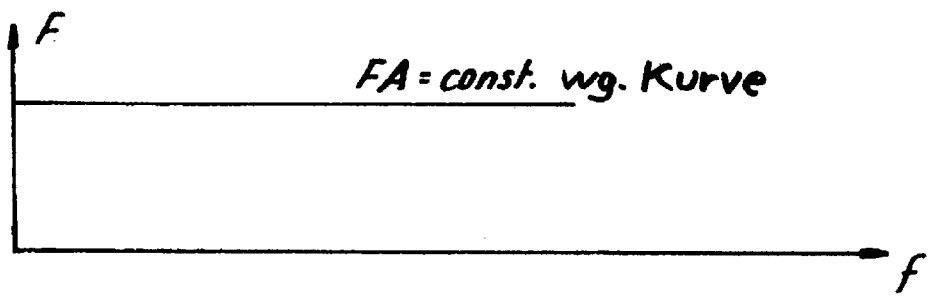

STAND, IN PARTICULAR FOR SURGICAL MICROSCOPES

CROSS-REFERENCE TO RELATED APPLICATIONS

The present application claims priority under 35 U.S.C. 119 of German Patent Application No. DE 200 19 109.8 filed Nov. 12, 2000.

The complete disclosures of the following three copending, commonly-owned U.S. patent applications filed concurrently with the present application are hereby incorporated by reference into the present specification: U.S. patent application Ser. No. 10/008285 (Attorney Reference LAGP:109_US_; corresponds to German Application No. 200 19 106.3 filed Nov. 12, 2000); U.S. patent application Ser. No. 10/007168 (Attorney Reference LAGP:110_US_, corresponds to German Application No. 200 19 107.1 filed Nov. 12, 2000); and U.S. patent application Ser. No. 10/010101 (Attorney Reference LAGP:111_US_; corresponds to German Application No. DE 200 19 105.5 filed Nov. 12, 2000).

FIELD OF THE INVENTION

The invention relates to a stand, more particularly to a stand for a surgical microscope which compensates for the weight of the microscope and any additional devices.

BACKGROUND OF THE INVENTION

It must be easy for surgical microscopes to be able to pivot over a wide, prescribed range. In addition, once a surgical microscope is properly positioned, the microscope stand should be capable of easily holding a microscope in the desired position. For this reason, microscope stands are provided with balance weights which compensate for the weight of the microscope and any additional devices. The balance weights are frequently arranged in the manner of beam-type balances. Particular embodiments of such beam-type balance arrangements are, for example, the "OHS™" design, in which balance weights are displaced from top to bottom via parallelogram carriers such that the overall centroid of the stand is situated in the lower region of the stand structure. The design principle of the OHS™ is illustrated symbolically in the International Patent Application WO 97/13997.

A further design, "MS 1" provides a balance device for ease of operability of the microscope and movability of the latter in space. This balance device also provides for the relevant compensation of changes in the weight of the microscope; adding or removing additional devices on the microscope is conducted via a pressure spring, which is clamped obliquely or diagonally in a parallelogram carrier. This parallelogram carrier serves as a pivotable horizontal carrier for the microscope. In the International Patent Application No. WO 99/1693 (Bees), the design of the MS 1 is illustrated symbolically and the particular parallelogram carrier design has been published in European Patent Application No. EP 433426 A1 (WO 91/472).

For the purpose of improved tilt stability, MS 1 provides a switchbox which contains the electric power supply for the microscope, its illuminating device, its controllers or the like and, if appropriate, any additional weight. The switchbox is mounted rigidly on the vertical support column of the stand and undertakes there only balancing over the vertical axis of the upright support column with regard to improving the tilting moment of the stand.

DE 19742050 A1 refers to an article "Gewichtsausgleich an feinmechanischen Geräten" ["Balancing on fine-mechanical equipment"], which was published by Hilpert in No. 2/1965 of the journal Feingerätetechnik, Volume 14. In this article from 1965, there is a detailed discussion of various weight-compensating measures in fine mechanics, which are achieved principally not by a counterweight, but by spring-compensating measures (such as, by way of comparison, only in the case of the MS 1 design).

DD 221571 A1 (1985) describes a stand design having a lever arm, which is weight-compensated by the spring which is connected to the lever arm via a cable pull. The surgical microscope is located at the distal end of the lever arm. The fundamental adjustment of this surgical microscope is performed via a threaded spindle which is used to draw the end of the spring fixed to the housing further from the lever arm, or to guide it nearer to it. Changes in weight at the microscope are compensated by the fact that the pivoting point of the cable pull is adjusted relative to the lever arm via a spindle. In order to achieve a uniform countermoment in all possible angular positions, it is necessary for the abovementioned point of action of the cable pull to be located on a connecting line between the axis of rotation of the lever arm and the centroid of the microscope. This is achieved by actuating an adjusting device in the form of a worm gear, which rotates a disc, connected to the lever arm, about the axis of rotation of the lever arm. This design requires a great number of adjusting measures in order to achieve the desired effect. In this case, the disc-worm design prevents, independently of the weight, the possibility of selecting any desired position of the microscope. Apart from this, the construction of this known design necessitates a high overall centroid of the stand, since all the balancing devices are arranged above the microscope.

DE 3739080 A1 (1989), likewise, specifies a spring device for balancing stands where cable pulls combined with springs are intended to lead to balancing. However, this publication discloses forcing support and adjustable movement which is exercised by an operator on a handle. This patent does not teach holding a load in a counterbalanced "floating state" as is desired when using a surgical microscope.

By contrast, U.S. Pat. No. 5,397,323 (1992) presents a surgical robot having parallelogram carriers, in the case of which, inter alia, the weight of the instrument is held in a weight-compensated fashion via a cable pull with the aid of a counterweight. The cable pull is of closed design in this case, that is to say that one cable in each case is guided from the instrument up to the counterweight over an upper and lower deflecting roller (FIG. 3 of U.S. Pat. No. 5,397,323). Such a design presupposes that the counterweight is attached in the immediate vicinity of the instrument. It could therefore be applied only poorly for use on a surgical microscope. Its technical teaching is therefore not obvious for adaptation to a stand for microscopes.

Stands without a pivoting arm but with balancing by means of tape pulls over a single deflecting roller directly on the support column were marketed under the designation "Standard" and "Universal". However, these had no pivoting arm, and the balancing is limited to equalizing the vertical load of the support arm directly on the support column. The tapes which transmitted the force run exclusively parallel to and immediately next to the support column. They act not on the support arm, but on a ring directly on the support column, which held the laterally projecting support arm. In the event of a change in load, it is necessary to change the balance weight if proper balance is desired.

DE 19742050 A1 (1999) discloses a stand design having a pivotable parallelogram carrier which is weight-compensated via a cable pull and a balancing spring such that the additionally present balance weights, which act in accordance with the abovementioned principle of the balance, can be designed to be particularly small. In this design, the cable pull is guided in a special way in order to minimize the balancing error, caused by the finite deflecting radius, in a wide pivoting range. The balancing error is, however, not eliminated by this measure, and so in specific pivoting positions it remains necessary to adjust the balance weights.

U.S. Pat. No. 6,070,839 (2000) discloses a further design having a pivoting arm and a cable pull-spring structure which permits pure balancing (in the sense of the abovementioned balancing with a diagonal bearing spring) but also without contributing balancing moments to an improvement in the tilt stability. In the case of changes in weight, the pivoting point of the cable pull is displaced, in a fashion comparable to the design in the abovementioned DD 221571, over a spindle.

U.S. Pat. No. 5,253,832 (1999) describes a stand having a centrally arranged tension spring for the balancing. This design offers no simple adjustability for changed loads, and so changes to a microscope or to its accessory equipment cannot lead directly to an adjustment of the equilibrants. In addition, it is disadvantageous that, as a function of the pivoting position of the support arm, the tension spring has a different degree of compression or expansion and, owing to the spring characteristic; this leads to different equilibrants and, thus, to a balancing response which differs over the pivoting range of the support arm and is therefore ineffective to a user in the surgical field.

BRIEF SUMMARY OF THE INVENTION

By contrast with these known designs, the object of the present invention is to create a novel stand, in particular, a stand for surgical microscopes, which, independently of the (pivoting) position of the microscope, effects an optimum possibility of compensation for changes to the load (surgical microscope) with the lowest possible outlay on adjustment.

This object is achieved by using a novel counterbalancing transmission which compensates a changed weight condition at the load (surgical microscope) by virtue of the fact that a constantly acting equilibrant (spring, weight or the like) affects the support arm of the load at a different transmission ratio, doing so independently of the position (pivoting position) of the load.

Various embodiments and developments of these embodiments occur within the scope of this fundamental idea of the invention as they are specified in the dependent claims and become evident to the person skilled in the art on the basis of the data, and if appropriate, taking account of the teachings of the patent applications of the same date mentioned below.

Springs are ideal for particularly powerful weight compensation in a small space. Both tension springs and pressure springs are suitable, depending on the attachment site. Springs which apply the same force over a specific compression or expansion path would be ideal in theory. However, such springs cannot be used in a comparable design having the comparable parameters. Consequently, use is preferably made of conventional springs which, however, tolerate a movement (pivoting high and low) of the load by means of compensation equalizing in the form of cams or the like, in order always to apply the same compensation force or compensation moments.

A design such that the device for generating a constant force is not a spring but a balance weight guided on a cable pull has proved to be another advantageous variant. Reference is made in this connection to U.S. patent application Ser. No. 10/010101 (Attorney Ref. LAGP:111__US__; corresponds to German Application No. DE 200 19 105.5 filed Nov. 12, 2000) which was filed on the same date and considers the particularities and further ideas of the invention, independent from the one above, in conjunction with balancing measures on a stand which are supported by cables and weights. If a design corresponding to U.S. patent application Ser. No. 10/010101 (Attorney Ref. LAGP:111__ US__; corresponds to German Application No. DE 200 19 105.5 filed Nov. 12, 2000) is selected, in addition to the weight-compensating effects, this also produces compensatory measures for improving the tilt stability of the stand.

Within the scope of the present application and without combination with the teaching of U.S. patent application Ser. No. 10/010101 (Attorney Ref. LAGP:111__US__; corresponds to German Application No. DE 200 19 105.5 filed Nov. 12, 2000), effects independent of tilting moment also occur in the case of a particular configuration of the counterbalancing transmission when the counterbalancing transmission is designed such that at least a portion of its mechanics is provided on the side of the vertical carrier diverted from the load, and that at least a portion of the device supplying the constant force is situated on the same side.

In addition to the abovementioned patent application U.S. patent application Ser. No. 10/010101 (Attorney Ref. LAGP:111__US__; corresponds to German Application No. DE 200 19 105.5 filed Nov. 12, 2000), the applications U.S. patent application Ser. No. 10/007168 (Attorney Reference LAGP:110__US__; corresponds to German Application No. 200 19 107.1 filed Nov. 12, 2000) and U.S. patent application Ser. No. 10/008285 (Attorney Reference LAGP:109__ US__; corresponds to German Application No. 200 19 106.3 filed Nov. 12, 2000) were also filed on the same date, all of these likewise referring to a stand design which, in a preferred embodiment, combines the combinations of features from these patent applications which are independent according to the invention.

With regard to their disclosure, the present and the abovementioned patent applications form a single entity, and the aim is for it to be possible to combine the elements illustrated in one and the other application with regard to subsequent applications in the sense of a completely novel stand concept in which the two inventions are united.

BRIEF DESCRIPTION OF THE DRAWINGS

The invention will now be described in more detail with reference to the appended drawings in which, in purely schematic fashion:

FIG. 2 shows the principle of the counterbalancing transmission;

FIG. 3 shows two diagrams, which illustrate the mode of operation of the spring unit in accordance with FIG. 1 for the purpose of generating a constant force;

DETAILED DESCRIPTION OF THE INVENTION

The figures are referred to in an overlapping fashion, identical reference symbols signifying identical components, reference symbols with the same numbers but different indices signifying slightly different components with identical tasks and/or similar effects. The reference symbols of the abovementioned patent applications U.S. patent application Ser. No. 10/010101 (Attorney Ref. LAGP:111_US_; corresponds to German Application No. DE 200 19 105.5 filed Nov. 12, 2000), U.S. patent application Ser. No. 10/007168 (Attorney Reference LAGP:110_ US_, corresponds to German Application No. 200 19 107.1 filed Nov. 12, 2000) and U.S. patent application Ser. No. 10/008285 (Attorney Reference LAGP:109_US_; corresponds to German Application No. 200 19 106.3 filed Nov. 12, 2000) filed on the same date are likewise to be found in this patent application, in order to be able to have access to a uniform list of reference symbols for the above-named case of a combination of these applications.

Figure 1:
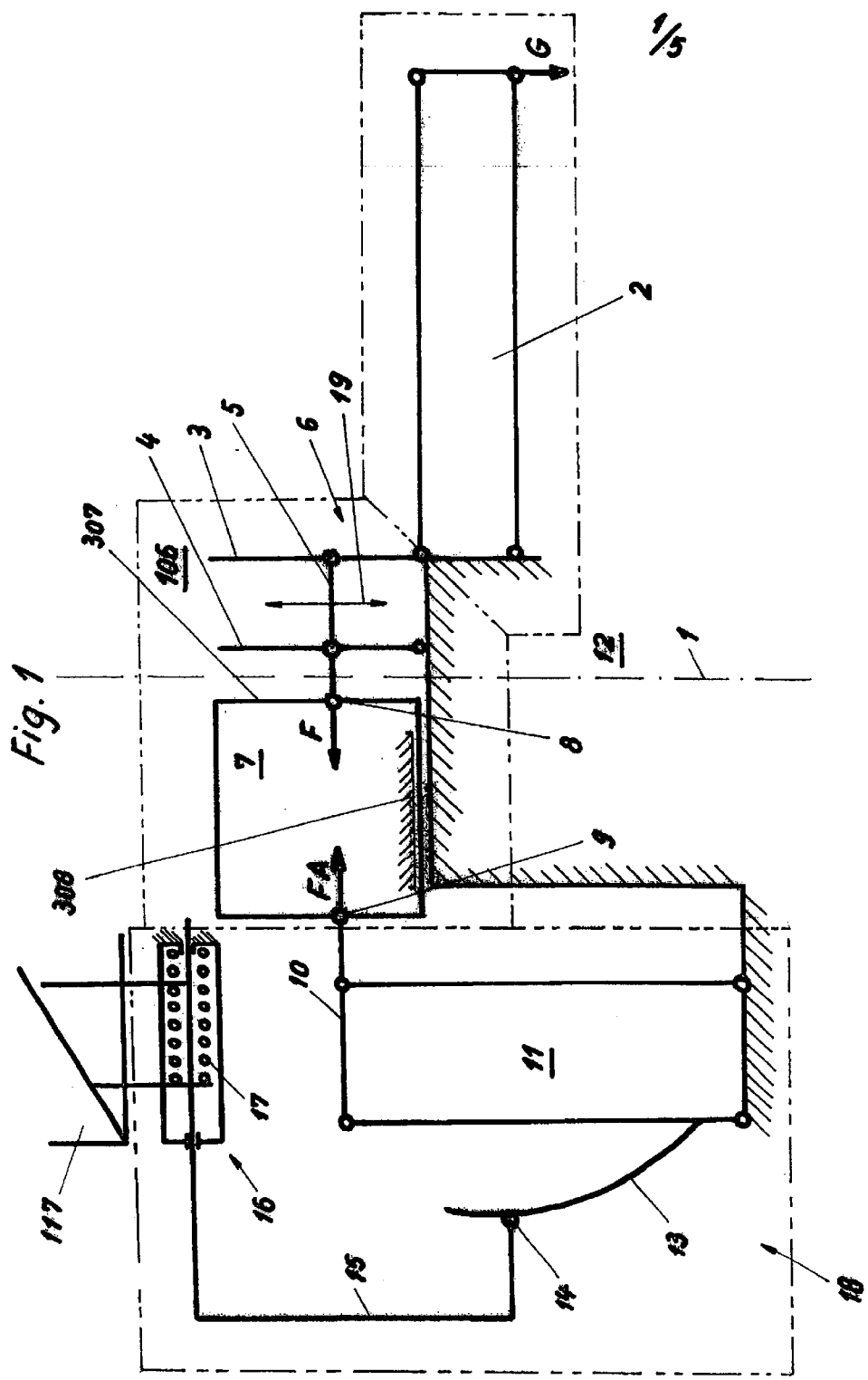
FIG. 1 shows the principle of the design of a balancing apparatus according to the invention, having spring-aided force compensation.

In FIG. 1, reference numeral 1 specifies the vertical axis of the vertical support of the stand and/or that axis about which the stand is examined for its tilt stability. This could be, for example, an axis which is vertical to the floor and runs through one of the support wheels of the stand. It follows in this case that this is a virtual axis, as a rule. This axis coincides, for example, with a tube axis of an upright tube of a microscope stand. It is then to be understood, for example, as a virtual axis when, for example, this upright tube can itself be pivoted (as in the case of OHS™, for example) or because the stand design could also manage entirely without a vertical upright tube (for example, in the case of a wall-supported stand).

Figure 4:
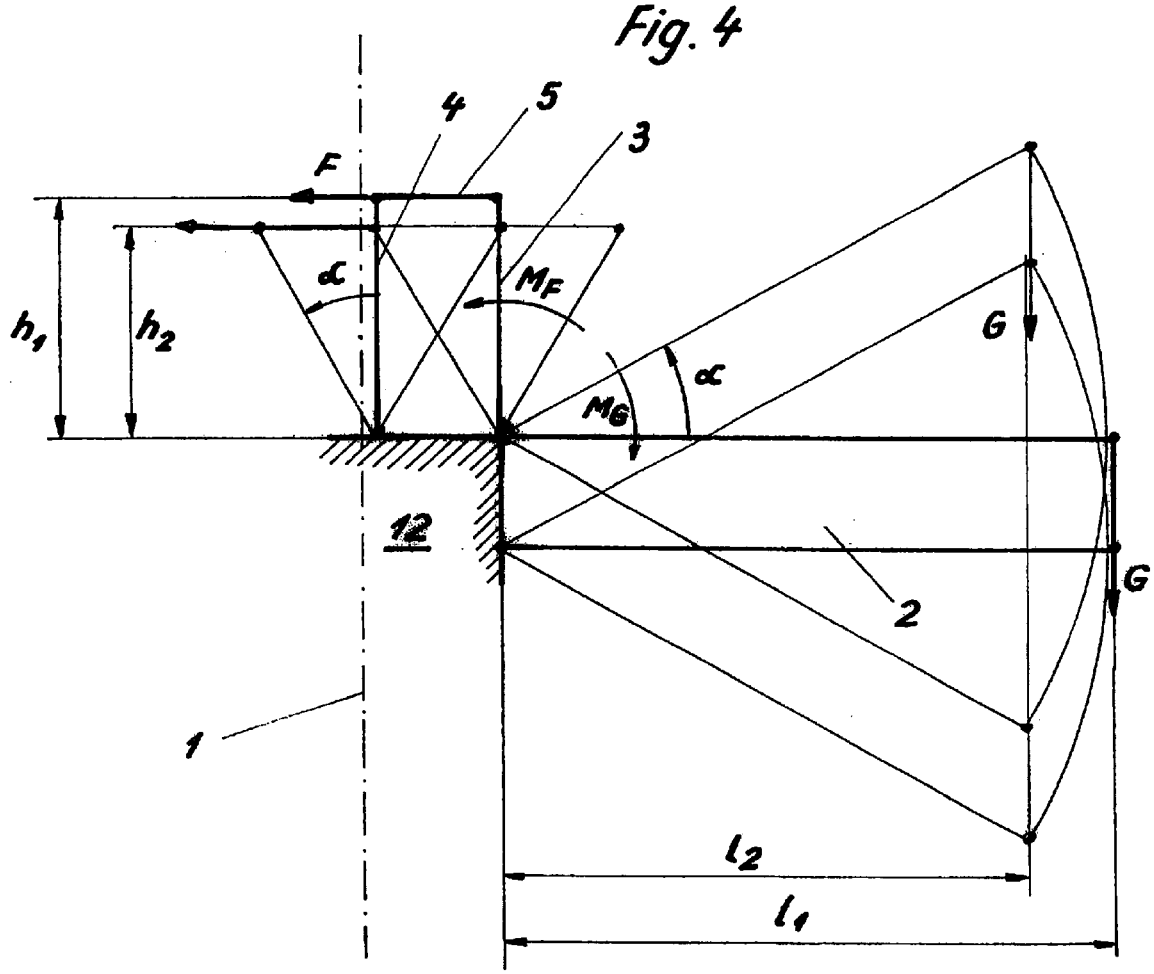
FIG. 4 shows the operating mechanism of the counterbalancing transmission according to the invention, as conditioned by the cam, for different pivoting positions of the stand.

The reference letter G specifies a load, or a surgical microscope, which is held at the distal end of a pivotable parallelogram carrier 2. The upper arm of the parallelogram carrier 2 is rigidly connected to a first arm 3 which is connected to a second parallelogram 6 with the aid of a second parallel arm 4 and a connecting arm 5. This parallelogram 6 forms the counterbalancing transmission 106 in which the level of the connecting arm 5 can be adjusted in its parallel position, as a result of which the geometry of the parallelogram can be varied (arrow 19). Pivoting the parallelogram carrier 2 upwards or downwards leads to pivoting of the parallelogram 6 to the left or to the right. FIG. 4 shows the outermost position of the connecting arm 5, in the case of which there is the largest lever arm transmission ratio, that is to say, for which G can assume the greatest load. Moreover, it may be seen from FIG. 4 how the geometry of the parallelogram 6 varies during the pivoting operation of the parallelogram carrier 2, the result being an automatic compensation effect in the case of the equilibrants.

This is so according to the formula M(G)=M(F) or l1×G= h1×F or l2×G=h1×F, M(G) specifying the moment of the load, and M(F) the moment of the counterforce.

l2=l1·cos α; and
h1=h1·cos α; thus $$\frac{l2}{h2} = \frac{l1 \cdot \cos\alpha}{h1 \cdot \cos\alpha} = \frac{l1}{h1}$$

In the case of a change in weight of G, it is therefore necessary according to the invention merely to displace the connecting arm 5 in parallel along the first arm 3 in order thereby to change h1 so that the compensation of the change in weight is achieved for a constant equilibrant FA.

Starting from the counterbalancing transmission 6, 106 (parallelogram), it is now possible for the most varied measures to be applied within the scope of the invention in order to achieve the constant equilibrant FA. On the one hand, these can be pendant weights which are connected to the connecting arm 5 over cable rollers (compare the above-mentioned patent application U.S. patent application Ser. No. 10/010101 (Attorney Ref. LAGP:111_US_; corresponds to German Application No. DE 200 19 105.5 filed Nov. 12, 2000)) but they can also be other forms of conventional force application such as, for example, springs (compare, for example, the design in accordance with U.S. Pat. No. 5,253,832 with its tension spring in the vertical support which, for such a variant, counts as being within the scope of this disclosure), electromotive, hydraulic or pneumatic force applicators or the like.

In the present exemplary embodiment according to FIG. 1, a carriage 7 or a slide is provided which, on the one hand supports a roller 8 which is rigidly connected to the connecting arm 5, and on the other hand supports a roller 9 which is connected to a second connecting arm 10 of a second parallelogram carrier 11. Like the parallelogram carrier 2 and the parallelogram 6, the second parallelogram carrier 11 is pivoted to a common supporting component, or basic body 12. The parallelogram carrier 11 has a control cam 13 on which there slides at least one roller 14 which is supported on an energy store 16 with the aid of a third connecting arm 15.

The energy store 16 can exhibit the most varied embodiments and does not limit the invention. Specified symbolically in the present case is a pressure spring 17 which, via the third connecting arm 15 and the roller 14 exerts a pull to the left on the second parallelogram carrier 11. This pull is transmitted as a force FA from the roller 9 onto the carriage 7, and by the latter over the roller 8 onto the connecting arm 5, the load G being compensated thereby.

A particular configuration of the control cam 13 permits the force FA always to be constant. This arises from the following context: when pivoted up from G or from the parallelogram carrier 2, the connecting arm 5 is displaced to the rear (left in the plane of the drawing). This causes displacement of the carriage 7 and of the second connecting arm 10 to the rear. As a result, the second parallelogram carrier 11 pivots rearwards and therefore gives way to the pressure spring 17, which is relieved. Because of the spring property, without a cam 13 this would lead to a decrease in the equilibrant FA, and thus to a reduction in the weight compensation (FIG. 3). Because of the design of the cam 13, however, this effect is balanced (compare FIG. 3), and so a constant equilibrant FA acts independently of the pivoting position of the load G. The hatched region on the right in FIG. 3 shows the non-compensated region for hmin, and the hatched region on the left shows the non-compensated region for hmax. The spring unit 18 is therefore designed as an apparatus for applying a constant force. As already mentioned, this apparatus can be replaced by other apparatuses for applying constant forces in order, in common with the counterbalancing transmission according to the invention, to render it possible to counterbalance the load G in a way according to the invention.

Given symbolically above the spring 17 is a diagram 117, which corresponds to that from FIG. 3.

Counting the carriage 7 as still belonging to the counterbalancing transmission 106, in specific embodiments a portion of the counterbalancing transmission can be situated to the left of the axis 1, while the spring unit 18 is situated entirely on the left-hand side. The dead weight of the carriage 7 and of the spring unit 18 is therefore distributed in these embodiments about the axis 1, such that the tilt stability over the axis 1 is not disadvantageously influenced.

Figure 5:
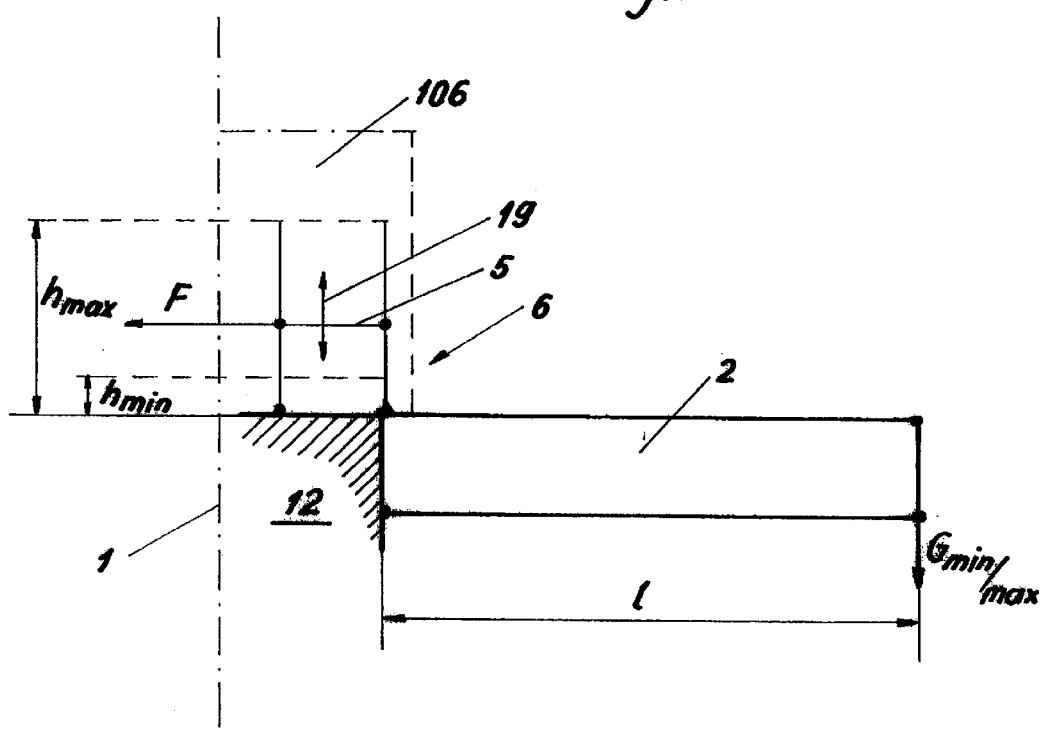
FIG. 5 shows a detail from FIG. 1.

The effect of the counterbalancing transmission is illustrated clearly in FIGS. 2 and 5.

$$G_{max} \cdot l = F \cdot h_{max} \text{ and } G_{min} \cdot l = F \cdot h_{min};$$

F being constant, as already mentioned. Given such a design according to the invention, the load G can be between G max=30 kp and G min=5 kp, for example.

In the drawings illustrated, parallelogram carriers and/or parallelograms are specified in each case, because these can be used favorably with regard to bending behavior and vibrations for the stand structure. However, the invention is not limited to parallelogram carriers, but could, rather, also function with the aid of normal bending carriers. This holds both for the support arm 2, from which the load G hangs, and for the parallelogram carrier 11 and the parallelogram 6, preference being given in the case of the latter to a parallelogram, in any case, for reasons relating to parallel guidance for the connecting arm 5.

It is not important within the scope of the invention whether the counterbalancing transmission 106 is arranged above, as illustrated, or below the parallelogram carrier 2. In the case of an arrangement which is below, therefore, the spring unit 18 is to be designed as a mirror image in that the pressure spring 17 would also need to be converted to a tension spring.

The top diagram in FIG. 3 specifies, by way of example, the approximate characteristic of the spring force in the case of a changed path (compression of the spring). This corresponds approximately to a normal pressure spring. The cam 13 is provided in order to modify the effect of this characteristic so that, as shown in the bottom diagram in FIG. 3, the force is constant at the point of action of the spring force, specifically at the carriage 7 and/or at the connecting arm 5. The effect of this cam is that the tractive force (FA) exerted on the connecting arm 10 and/or the carriage 7 remains constant in the case of a pivoting position of the load G and a pivoting position, associated therewith, of the counterbalancing transmission 106 and a pivoting position, associated therewith, of the parallelogram carrier 11 and compression or decompression, associated therewith, of the spring 17.

This mechanical design is accompanied by the effect that, given the same path of the support arm 2, the carriage 7 travels different distances as a function of the load G, if the latter is compensated by setting the counterbalancing transmission 106.

Figure 6:
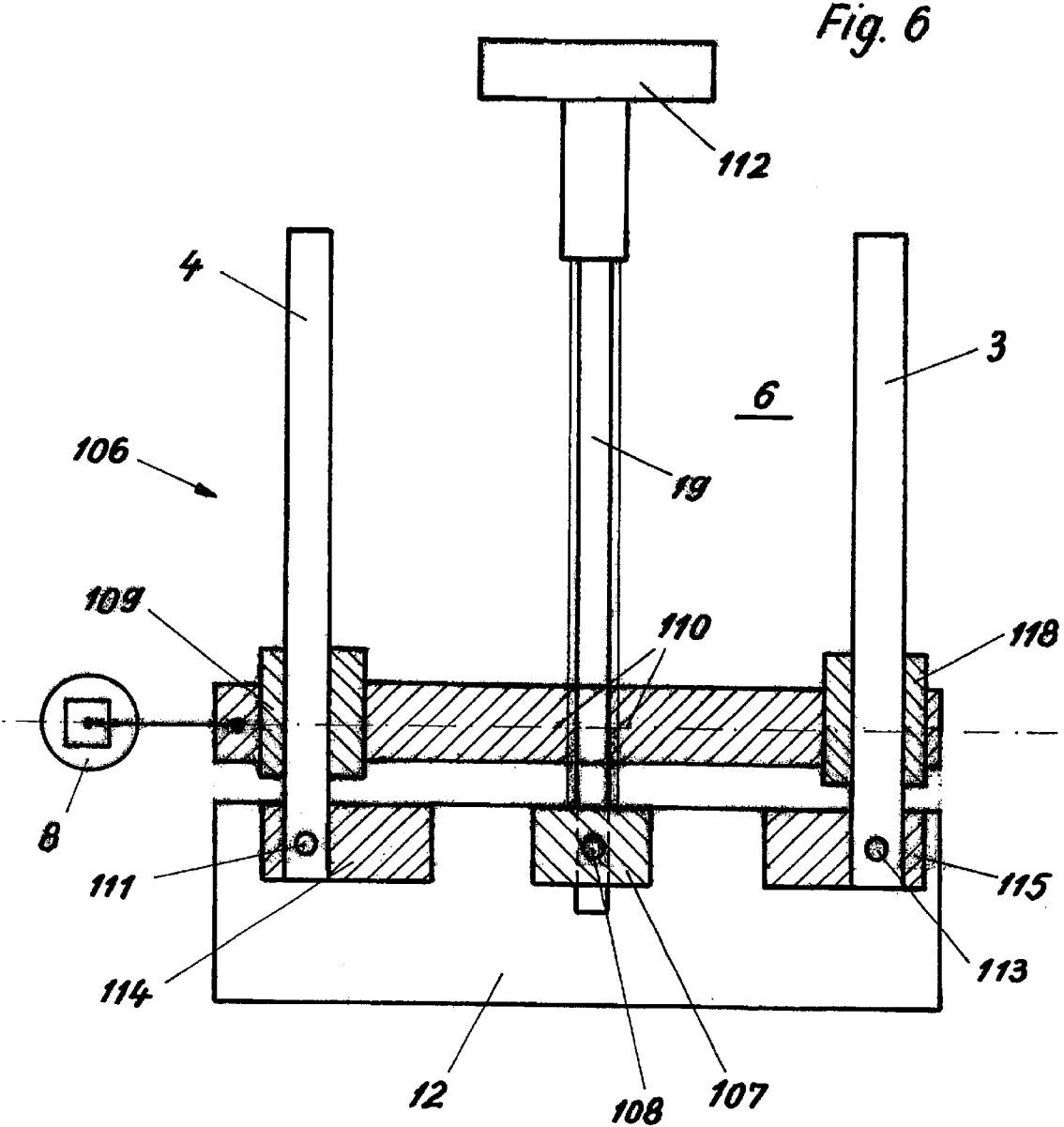
FIG. 6 shows a possible structural design of the counter-balancing transmission.

The design presented in FIG. 6 comprises the parallelogram arms 3 and 4 which are pivotably mounted on the basic body 12 via pivoting holders 115 and 114, respectively. They support parallel guides 109 and 118, respectively, for the connecting arm 5 which, for its part, has a threaded bore 110 for the adjusting spindle 19. The latter bears at its upper end a handle 112 but, as already mentioned, it could also be driven by a motor. The spindle 19 is mounted at its lower end on the basic body 12 via a pivot bearing 107. Adjusting spindles 116 serve to adjust the connecting arm 5 in a parallel fashion with reference to the basic body 12.

The following list of reference symbols is a part of the description. The super structures specified in the patent claims are considered to be disclosed just as they occur in the description. Carriers in the sense of the patent claims are to be understood both as individual support arms and as parallelogram carriers or similar structures.

List of Reference Symbols

1—Vertical axis of the vertical support
2—Pivotable parallelogram carrier/support arm
3—First arm
4—Second arm
5—First connecting arm
6—Parallelogram carrier and/or 106-counterbalancing transmission
7—Transfer element, preferably carriage or slide
8—Roller
9—Roller
10—Second connecting arm
11—Second pivotable parallelogram carrier/support arm
12—Basic body
13—Control cam
14—Roller
15—Third connecting arm
16—Energy store
17—Pressure spring
18—Load-equalizing unit
19—Spindle
20—Stand foot
21—Upright tube
106—Counterbalancing transmission (compare 6)
107—Pivot bearing
108—Pivoting axes for pivot bearings
109—Parallel guides
110—Threaded bore
111—Pivoting axes for pivot bearings
113—Pivoting axes for pivot bearings
114—Pivot bearing
115—Pivot bearing
112—Handle
117—Force-displacement diagram of the spring 17
118—Parallel guides
307—Cheek of the carriage 7
308—Guide for carriage
G—Load and/or weight of the microscope
AG—Balance weight
F—Force
FA—Constant balance force

What is claimed is:

1. In a stand having a pivotable parallelogram carrier for supporting a load at a distal end thereof and a load-equalizing unit connected to said parallelogram carrier for compensating said load with respect to said parallelogram carrier, the improvement comprising:

said load-equalizing unit acting in an equalizing direction at a constant force independently of said load; and a counterbalancing transmission between said load-equalizing unit and said parallelogram carrier for varying a point of action of said constant force on said parallelogram carrier relative to a pivot point of said parallelogram carrier, said counterbalancing transmission including a first arm rigidly connected to said parallelogram carrier and on which said point of action is located, wherein a counterbalancing moment about said pivot point produced by said constant force corresponds to a loading moment about said pivot point produced by said load.

2. The improvement according to claim 1, wherein said load equalizing unit is connected to said counterbalancing transmission by a transfer element displaceable in a direction of force, said counterbalancing transmission includes a first connecting arm attached to said transfer element in a manner which allows for movement of an attachment location of said first connecting arm with respect to said transfer element, and said load equalizing unit includes a second connecting arm attached to said transfer element in a manner which allows for movement of an attachment location of said second connecting arm with respect to said transfer element.

3. The improvement according to claim 1, wherein said parallelogram carrier includes an upper member and a lower member parallel to said upper member, and said first arm of said counterbalancing transmission is rigidly attached to said upper member.

4. The improvement according to claim 2, further comprising a basic body forming a common supporting component for said parallelogram carrier and said counterbalancing transmission, wherein said first connecting arm is adjustable along said first arm of said counterbalancing transmission via a threaded spindle connected to said basic body.

5. The improvement according to claim 1, wherein said counterbalancing transmission includes a force-transmitting first connecting arm connected to said first arm, and said load equalizing unit comprises means for applying force to said first connecting arm.

6. The improvement according to claim 5, wherein said means for applying force includes a spring.

7. The improvement according to claim 5, wherein said means for applying force includes a pendant weight.

8. The improvement according to claim 5, wherein said means for applying force includes an electromotive force applicator.

9. The improvement according to claim 5, wherein said means for applying force includes a hydraulic force applicator.

10. The improvement according to claim 5, wherein said means for applying force includes a pneumatic force applicator.

11. The improvement according to claim 3, wherein said first arm extends at a right angle to said upper arm of said parallelogram carrier.

12. The improvement according to claim 2, further comprising a basic body forming a common supporting component for said parallelogram carrier and said counterbalancing transmission, wherein said counterbalancing transmission is in the form of a parallelogram linkage, said linkage including said first arm and a second arm parallel to said first arm, said first and second arms each being pivotably attached to said basic body and said first connecting arm being movably mounted on said first and second arms for parallel displacement along said first and second arms.

13. The improvement according to claim 2, wherein said transfer element is a carriage.

14. The improvement according to claim 13, wherein said first connecting arm is connected to said carriage by a roller for rolling along an end of said carriage.

15. The improvement according to claim 13, wherein said second connecting arm is connected to said carriage by a roller for rolling along an end of said carriage.

16. The improvement according to claim 13, wherein said load-equalizing unit comprises a parallelogram linkage transmitting force to said carriage via said second connecting arm, a control cam rigidly connected to said parallelogram linkage, a spring for acting on said control cam, and a third connecting arm through which said spring acts on said control cam.

17. The improvement according to claim 16, further comprising a basic body forming a common supporting component for said parallelogram carrier and said counterbalancing transmission, wherein said parallelogram linkage of said load-equalizing unit comprises a pair of elongated parallel arms each having one end pivotably attached to said basic body and an opposite end pivotably attached to said second connecting arm.

18. The improvement according to claim 1, further comprising a vertical supporting axis about which said stand is examined with regard to tilt stability, wherein said load-equalizing unit and said counterbalancing transmission are situated at least partially on one side of said vertical supporting axis, and said parallelogram carrier is located on an opposite side of said vertical supporting axis.

19. The improvement according to claim 13, further comprising a cable pull connected at one end to said carriage, a roller over which said cable pull is deflected downwards, and a balance weight suspended in a freely movable fashion as to its level at another end of said cable pull.

20. The improvement according to claim 16, wherein said control cam is configured such that despite pivoting of said a parallelogram linkage of said load-equalizing unit, it is possible to transfer a constant tractive force from said second connecting arm.

21. The improvement according to claim 4, wherein said spindle is rotated to adjust for a change in said load.

22. The improvement according to claim 21, further comprising a sensor for determining said change in said load and a computer connected to said sensor for controlling adjustment rotation of said spindle.

23. The improvement according to claim 22, wherein said sensor is a shear force sensor arranged at a weakened location on a non-supporting arm of said parallelogram carrier.

24. The improvement according to claim 16, further comprising a brake arranged at a bearing point of one of said parallelogram carrier, counterbalancing transmission, said carriage, and said parallelogram linkage of said load-equalizing unit for braking said stand in a selected position.

25. The stand according to claim 24, wherein said brake is an automatically driven brake.

26. An apparatus for generating a constant force for balancing a load on a stand, said apparatus comprising:
 a base;
 a parallelogram linkage including a pair of elongated parallel support arms pivotally attached to said base and a connecting arm pivotally attached to each of said pair of support arms;
 a spring connected to said parallelogram linkage for applying a spring force to said parallelogram linkage, said spring force being transmitted along said connecting arm; and
 a compensation cam between said spring and said parallelogram linkage for keeping said applied spring force constant as a function of the angular position of said support arms of said parallelogram linkage, said compensation cam transmitting said applied spring force to said parallelogram linkage at a fixed location on the parallelogram linkage.

* * * * *